United States Patent [19]
Ball et al.

[11] Patent Number: 5,679,580
[45] Date of Patent: Oct. 21, 1997

[54] RAPID EVAPORATION METHOD FOR ANALYSIS

[75] Inventors: Carroll E. Ball, Kansas City, Mo.; Paul G. Gorman, Prairie Village, Kans.; Michael F. Fischer, Lee's Summit, Mo.; Brian R. Cage, Shawnee, Kans.; David H. Steele, Kansas City, Mo.

[73] Assignee: Midwest Research Institute, Kansas City, Mo.

[21] Appl. No.: 528,131

[22] Filed: Sep. 14, 1995

Related U.S. Application Data

[63] Continuation of Ser. No. 208,446, Mar. 9, 1994, abandoned.

[51] Int. Cl.⁶ ........................................ G01N 1/00
[52] U.S. Cl. ........................................ 436/177; 436/174
[58] Field of Search ................ 55/235–238, 270, 55/459.1; 73/863.12, 863.21; 95/220; 261/79.2; 436/174, 177; 34/594, 326

[56] References Cited

U.S. PATENT DOCUMENTS

| | | | |
|---|---|---|---|
| 3,324,632 | 6/1967 | Berneike et al. | 55/236 |
| 3,642,983 | 2/1972 | Viola | 424/553 |
| 3,714,342 | 1/1973 | Kabisch | 423/588 |
| 4,092,845 | 6/1978 | Prodi et al. | 73/863.21 |
| 4,117,714 | 10/1978 | Goodson et al. | 55/238 X |
| 4,410,710 | 10/1983 | Berkowitz et al. | 549/312 |
| 4,479,379 | 10/1984 | Tarcy | 436/177 X |
| 4,532,155 | 7/1985 | Golant et al. | 34/594 X |
| 4,950,664 | 8/1990 | Goldberg | 514/219 |
| 5,011,517 | 4/1991 | Cage et al. | 73/863.21 |
| 5,100,623 | 3/1992 | Friswell | 422/68.1 |
| 5,189,811 | 3/1993 | Rose et al. | 34/326 X |
| 5,202,426 | 4/1993 | Strumwasser et al. | 536/23.2 |

FOREIGN PATENT DOCUMENTS

| | | |
|---|---|---|
| 2506971 | 9/1976 | Germany. |
| 3-143505 | 6/1991 | Japan. |

OTHER PUBLICATIONS

H.C. Hansson et al. *Nucl. Instrum. Methods Phys. Res., Sect.* B1984, 231, 158–62.
J.G. Brennan et al. *Chem. Abstr.* 1972, 77, 36972x.
W. Stoeber et al. *Chem. Abstr.* 1973, 79, 82974p.
H.C. Hansson et al. *Chem. Abstr.* 1984, 101, 136683m.
P. Goldbach et al. *Chem. Abstr.* 1994, 120, 14750c.

*Primary Examiner*—Arlen Soderquist
*Attorney, Agent, or Firm*—Chase & Yakimo

[57] ABSTRACT

Dissolved components of a liquid sample are recovered for analysis by delivering the sample to a concentrator comprising a cylindrical receptacle into which an uncontaminated gas, such as air, is introduced in a direction tangentially of the cylindrical wall. The gas is under sufficient pressure to effect swirling of the gas and liquid sample and atomization of the sample to rapidly evaporate the same and cause a residue containing the dissolved components to be deposited on the interior surface of the wall. A reconstituting solvent is then admitted to the receptacle to dissolve the residue and provide a reconstituted, concentrated sample for analysis. If desired, the sample may be concentrated to a given volume rather than to complete dryness. In nonlaboratory applications, a dilute liquid substance may be processed by rapid evaporation to provide a final product of desired concentration.

3 Claims, 2 Drawing Sheets

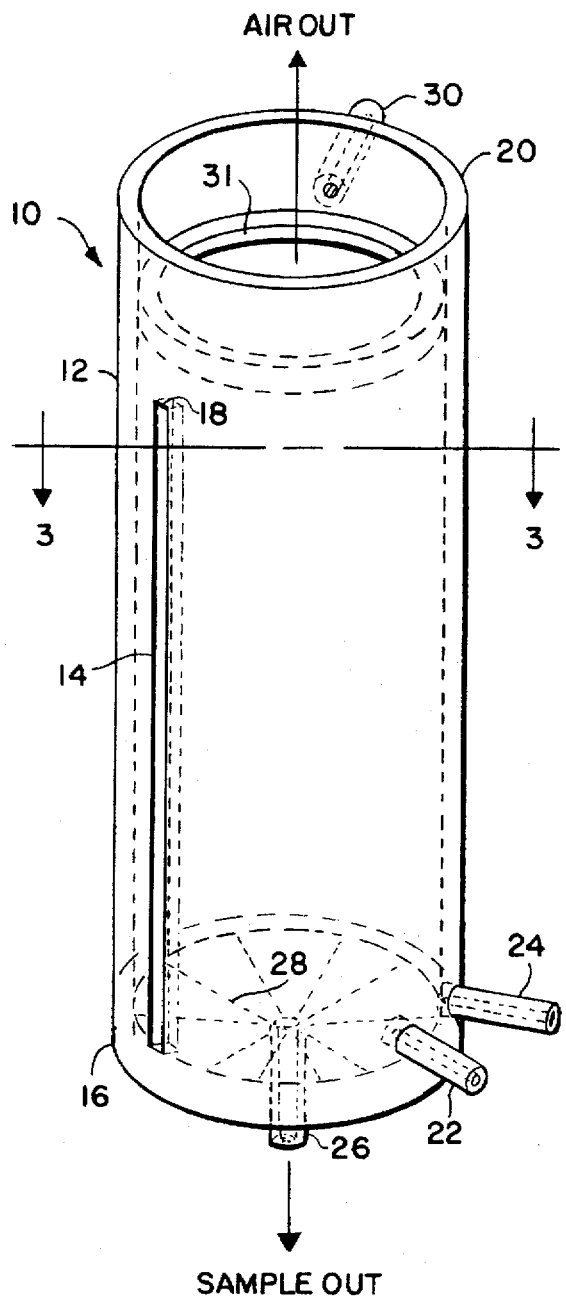
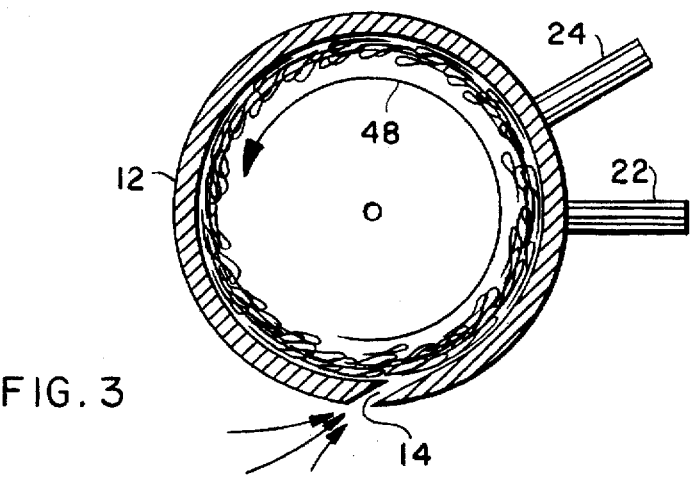

1

RAPID EVAPORATION METHOD FOR ANALYSIS

This application is a continuation of application Ser. No. 08/208,446, filed Mar. 9, 1994, now abandoned.

BACKGROUND AND SUMMARY OF THE INVENTION

This invention relates to an improved method and apparatus for rapidly evaporating a relatively dilute liquid substance to provide a final product of desired concentration, and to the processing of liquid samples to recover for analysis components dissolved therein.

Laboratory analysis of liquid samples involves the time consuming step of initially concentrating a sample by reducing its volume through evaporation. The volume reduction increases the concentration of the sample and permits analysis of the contents of the sample by conventional laboratory procedures. Systems for sample concentration in present use include evaporators which typically operate in a batch mode and agitate and/or heat the sample to increase the speed of evaporation. However, a period of several hours or even a day is typically required to reduce the fluid sample volume to the desired concentration. This severely limits the rate at which laboratory procedures can be concluded. Sample analysis is widely employed in many fields including environmental applications such as water testing and air monitoring, soil testing and the determination of pharmaceutical purity.

The present invention, therefore, is directed to an improved process for evaporating liquid samples that will enable analytical laboratories to meet requirements for rapid sample turnaround and provide the ability to process large volume samples on a continuous as well as a batch basis. The invention is further directed to the concentration of any relatively dilute liquid substance by rapid evaporation thereof to provide a final product of desired concentration, either for analysis or to obtain a high concentration for other advantageous purposes such as in the preparation of concentrated food products.

It is, therefore, an important object of the present invention to provide a method of evaporating a liquid substance at a high rate in order to provide a final product of desired concentration or reduce the substance to a dry residue, depending upon the result desired in a particular application.

Another important object of the invention is to provide a method and apparatus for processing a liquid sample to recover for analysis components dissolved therein, by subjecting the sample to a gas under sufficient pressure to effect swirling of the gas and liquid sample and atomization of the sample to rapidly evaporate the same.

Still another important object is to provide a method and apparatus for processing a liquid sample to recover for analysis components dissolved therein, wherein the sample is subjected to a gas under sufficient pressure to effect swirling of the gas and liquid sample and atomization of the sample to rapidly evaporate the same and cause a residue containing the dissolved components to be deposited upon a wall of a receptacle containing the gas and sample, the residue being recovered by a reconstituting solvent to provide a reconstituted sample for subsequent analysis.

Furthermore, it is an important object of this invention to provide a method and apparatus for processing a relatively dilute liquid substance by subjecting the same to an uncontaminated, swirling gas under a pressure sufficient to atomize the swirling liquid and effect rapid evaporation to reduce the volume thereof until a final product of desired concentration is obtained.

Another important object is to provide a method and apparatus as set forth in the last mentioned object for processing liquid substances comprising either samples to be subjected to analysis or liquids which are to be increased in concentration or evaporated to dryness for other purposes.

Still another important object of the present invention is to provide a receptacle having a generally cylindrical wall and which provides a means for contacting a gas with a liquid to effect swirling of the same and facilitate the atomization of the swirling liquid to effect rapid evaporation thereof.

Other objects will become apparent as the detailed description proceeds.

DESCRIPTION OF THE DRAWINGS

FIG. 2 is a perspective view of the cylindrical receptacle of FIG. 1 as seen from the opposite side.

FIG. 3 is a horizontal cross section of the receptacle taken along line 3—3 of FIG. 2 and shows the swirling liquid adjacent the interior wall surface, the arrows indicating air flow into the inlet slit and within the receptacle.

DETAILED DESCRIPTION

Figure 1:
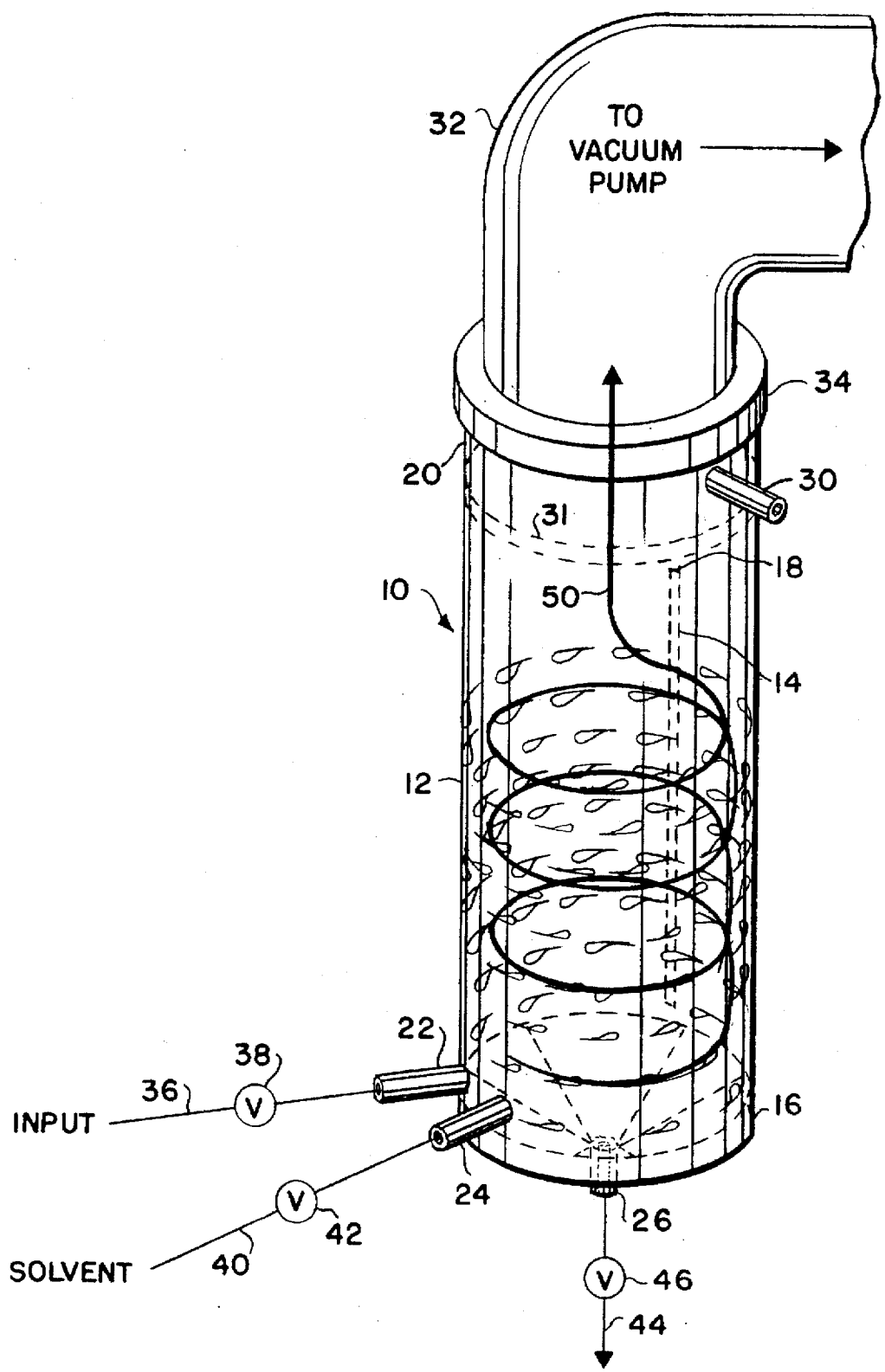
FIG. 1 is a perspective, partially diagrammatic view of a concentrating apparatus including a cylindrical receptacle into which a gas under pressure and a liquid are introduced, and illustrates the swirling of the liquid within the container under the action of the pressurized gas.

Referring initially to FIGS. 2 and 3, an upright cylindrical receptacle 10 is preferably constructed of Teflon, glass or stainless steel and presents a relatively thin, cylindrical wall 12 having an elongated, vertical inlet slit 14 therein extending from a circular base plate 16 to a termination 18 spaced from the upper end 20 of the receptacle 10. A pair of closely spaced, outwardly projecting inlet ports 22 and 24 communicate with the interior of the cylindrical chamber defined by the wall 12, and are disposed in closely spaced relationship to the base plate 16. An outlet port 26 is located at the center of the base plate 16, the latter sealing the bottom of the receptacle 10 and providing an upper surface 28 which has an inverted conical configuration presenting approximately at twenty degree slope from the circumferential edge of plate 16 to outlet port 26. A pressure sensor port 30 also communicates with the interior of the cylindrical chamber and is disposed above inlet slit 14 adjacent the upper end 20 of the receptacle 10. An annular ridge 31 is presented by a ring on the interior wall of the chamber located between the upper end 18 of slit 14 and the port 30.

Referring to FIG. 1, it may be seen that the receptacle 10 is part of a concentrating system that supplies a liquid and a gas to the receptacle and establishes a pressure differential across the inlet slit 14. More particularly, a tube or conduit 32 communicates with a cap 34 which fits over and is sealed to the upper end 20 of the receptacle 10, the conduit 32 extending to the intake of a vacuum pump (not shown). An input liquid supply line 36 communicates with inlet port 22 through a valve 38, and a solvent supply line 40 communicates with the other inlet port 24 via valve 42. An outlet line 44 extends from port 26 and is controlled by a valve 46.

The concentrating system of FIGS. 1–3 may be employed in various ways depending upon a particular application. One operational mode is the processing of a liquid sample to recover components dissolved therein, as a first step in an analytical laboratory procedure in which the dissolved components are to be identified. In this mode, the liquid sample is supplied by line 36 and admitted to the cylindrical chamber within receptacle 10 by opening the valve 38. With the vacuum pump in operation, a negative pressure at the top of receptacle 10 draws ambient air or a controlled atmosphere, such as nitrogen, into the chamber through the Venturi-like inlet slit 14. This causes the air or other gas to be introduced into the cylindrical chamber in a tangential direction where it is caused to swirl around the inside surface of the cylindrical wall 12 as illustrated by the arrow 48 in FIG. 3. The motion of the air is similar to that as described in U.S. Pat. Nos. 4,117,714 and 5,011,517 owned by the assignee herein, such patents also disclosing a cylindrical receptacle into which air is introduced in a direction tangentially of the cylindrical wall by a vacuum pump connected to the upper end of the cylinder.

The liquid sample contains dissolved components to be recovered for analysis. The function of the incoming air or other gas is to effect rapid evaporation of the sample and cause a residue containing such components to be deposited on the interior surface of the wall 12. This is accomplished in the present invention by maintaining the incoming air, injected into the chamber through inlet slit 14, at a sufficiently high pressure to effect swirling of the gas and liquid sample and atomization of the sample into fine droplets so that evaporation will occur at a much higher rate than it would if the liquid were simply contacted by the air and swirled in the chamber. The air and liquid swirl within the chamber as indicated by the arrow 48 (FIG. 3), forcing the atomized liquid against the interior surface of the wall 12 as the air and liquid spin on the cylindrical wall. As illustrated in FIG. 1, the air spirals upwardly (arrow 50) to the vacuum conduit 32 and thus flows from the receptacle 10 while the liquid advances to approximately one-half of the height of the receptacle. The applied vacuum is limited to a level which will cause the atomization necessary for rapid evaporation, but not suck the liquid out of the receptacle 10. The ridge 31 provides a barrier to further upward movement of viscous materials that may be present on the interior surface of the wall 12.

Once the receptacle 10 is charged with the sample to be evaporated, valve 38 is closed and the vacuum is maintained until evaporation is complete. This leaves the dissolved components of the sample deposited on the interior surface of the wall 12. Valve 42 is then opened to admit a reconstituting solvent through inlet port 24 which is swirled briefly to dissolve the sample residue from the wall surface. The vacuum is then removed and valve 46 is opened to drain the reconstituted sample from the receptacle 10. Examples of recovery using the method of the present invention are given below.

EXAMPLE 1

A 15 milliliter sample of an aqueous solution of sodium chloride was evaporated and then reconstituted. The cylindrical receptacle 10 utilized had an inside diameter of 1.75 inches. The inlet slit 14 was 4.5 inches long and 0.06 inches wide. Complete evaporation was accomplished in 12 minutes utilizing ambient air as the atomizing gas introduced into the inlet slit 14 at a rate of approximately 20 to 30 cubic feet per minute at standard conditions (20° C., 1 atmosphere). The sample solution was very dilute (0.17 percent by weight NaCl), and 98 to 100 percent of the NaCl was recovered from the deposited residue. Distilled water was used as the reconstituting solvent. Evaporation was conducted at ambient temperature.

EXAMPLE 2

The same receptacle configuration and airflow rate were employed as in Example 1. The sample was an ethanol solution of theophylline, 25 milliliters, 0.2 mg. per ml. of ethanol. The evaporation time was ten minutes and, using water as the reconstituting solvent, 85 percent recovery of the theophylline was obtained. Using ethanol as the reconstituting solvent, the recovery was 100 percent. Evaporation was conducted at ambient temperature.

EXAMPLE 3

The same airflow rate and a similar receptacle configuration were employed as in Example 1. The width of the inlet slit 14 was 0.05 inch. The sample evaporated comprised 25 ml. of an ethyl acetate extraction of an aqueous solution of organic matter. The 25 ml. extraction included 1.8 mg. of Virginiamycin as the marker compound. The evaporation time was less than two minutes and, using dimethyl sulfoxide as the reconstituting solvent, 75 percent recovery of the Virginiamycin was readily obtained. Evaporation was conducted at ambient temperature and analysis of the recovery was by HPLC (liquid chromatigraph).

It should be understood that in the process of the present invention the air or other gas employed to cause rapid evaporation is uncontaminated, i.e, free from any particulate matter or other contaminants that could be deposited on the interior wall surface of the cylindrical receptacle and invalidate the subsequent analysis of the residue from the liquid sample. The selection of an atomizing gas will be determined by the sample under investigation. The inlet airflow rate will vary in accordance with the width of the slit 14.

A second mode of operation of the concentrating system of the present invention is similar to that as described above for the first operational mode, except that a reconstituting solvent is not employed. A dilute liquid substance is supplied from line 36 and vacuum is applied until the volume of the liquid is reduced to the desired final concentration. Liquid food products and the like may be concentrated by this process. A much larger capacity receptacle would typically be employed as compared to use of the process for laboratory applications discussed above. Concentration of a sample to a given volume, rather than to complete dryness as in Examples 1, 2 and 3 above, may also be selected for laboratory sample processing if desired.

In utilizing the present invention to concentrate a liquid to a given volume, pressure differential may be employed as feedback to indicate when the desired volume has been attained. The pressure sensor port 30 is provided for this purpose to facilitate monitoring of the pressure drop, the reduction thereof to a predetermined value being indicative of a corresponding volume decrease due to the lower resistance to the flow of gas into the receptacle through the inlet slit 14.

Having thus described the invention, what is claimed as new and desired to be secured by Letters Patent is as follows:

1. A method of processing a liquid sample to recover for analysis components dissolved therein, said method comprising the steps of:

delivering said sample to a receptacle having a generally cylindrical wall presenting an interior surface;

introducing gas into said receptacle tangentially of said wall under sufficient pressure to effect swirling of the gas and liquid sample and atomization of the sample to rapidly evaporate the same and cause a residue containing said components to be deposited on said surface; and thereafter admitting a reconstituting solvent to said receptacle; and flowing additional gas into said receptacle tangentially of said wall to swirl the solvent in the receptacle and cause the solvent to contact said surface and dissolve the residue in the solvent, whereby to provide a reconstituted sample; and withdrawing the reconstituted sample from the receptacle for subsequent analysis to determine the identity of the components.

2. The method as claimed in claim 1, further comprising the step of exhausting the gas from the receptacle after contact with the sample, whereby the gas flows into and out of the receptacle while the unevaporated sample remains therein.

3. A method of processing a liquid sample to recover for analysis components dissolved therein, said method comprising the steps of:

delivering said sample to a receptacle having a generally cylindrical wall presenting an interior surface;

flowing gas into said receptacle tangentially of said wall to contact the gas with the liquid sample and effect swirling of the gas and liquid sample within the receptacle;

maintaining said gas under a pressure sufficient to atomize the swirling liquid sample and effect rapid evaporation thereof to dryness and the deposit of a dry residue on said interior surface; and thereafter admitting a reconstituting solvent to said receptacle; and flowing additional gas into said receptacle tangentially of said wall to swirl the solvent in the receptacle and cause the solvent to contact said surface and dissolve the residue in the solvent, whereby to provide a reconstituted sample; and withdrawing the reconstituted sample from the receptacle for subsequent analysis to determine the identity of the components.

* * * * *